(12) United States Patent
Blyth et al.

(10) Patent No.: US 6,689,316 B1
(45) Date of Patent: Feb. 10, 2004

(54) HOLOGRAPHIC SENSORS AND THEIR PRODUCTION

(75) Inventors: Jeffrey Blyth, Cambridge (GB); Christopher Robin Lowe, Cambridge (GB); Andrew Geoffrey Mayes, Cambridge (GB); Roger Bradley Millington, Cambridge (GB)

(73) Assignee: Cambridge University Technical Services, Ltd. (GB)

(*) Notice: Subject to any disclaimer, the term of this patent is extended or adjusted under 35 U.S.C. 154(b) by 0 days.

(21) Appl. No.: 09/701,476

(22) PCT Filed: May 21, 1999

(86) PCT No.: PCT/GB99/01612

§ 371 (c)(1),
(2), (4) Date: Feb. 9, 2001

(87) PCT Pub. No.: WO99/63408

PCT Pub. Date: Dec. 9, 1999

(30) Foreign Application Priority Data

May 29, 1998 (GB) ................................ 9811655

(51) Int. Cl.⁷ ................ G01N 31/22; G01N 15/06; G01N 31/00; G03H 1/02; G03H 1/04
(52) U.S. Cl. ............... 422/56; 422/50; 422/60; 422/68.1; 436/2; 436/8; 436/43; 436/164; 436/501; 436/518; 359/3; 430/1; 430/2
(58) Field of Search .................. 422/50, 56, 61, 422/68.1, 82.05, 82.08, 82.09; 436/501, 518, 2, 8, 43, 164; 359/3; 430/1, 2, 568; 435/6

(56) References Cited

U.S. PATENT DOCUMENTS

| 3,776,727 A | * | 12/1973 | Nassenstein et al. ........... 430/1 |
| 4,720,441 A | * | 1/1988 | Clark et al. .................... 430/1 |
| 4,804,599 A | * | 2/1989 | Ficken ........................... 430/2 |
| 4,836,628 A | * | 6/1989 | Doyle et al. ................... 359/3 |
| 5,264,338 A | * | 11/1993 | Urabe et al. ................. 430/568 |
| 5,352,582 A | * | 10/1994 | Lichtenwalter et al. ........ 435/6 |
| 5,633,100 A | * | 5/1997 | Mickish et al. ................. 430/1 |
| 5,716,679 A | | 2/1998 | Krug et al. |

FOREIGN PATENT DOCUMENTS

| GB | WO 95/26499 | * 10/1995 | .......... G01N/21/75 |
| WO | 8807203 | 9/1988 | |
| WO | 9526499 | 10/1995 | |

OTHER PUBLICATIONS

Liesegang, Raphael Ed. "A bath process for producing Lippmann plates" Photographische Rundschau, vol. 52, 1915, pp. 198–200.

* cited by examiner

Primary Examiner—Jill Warden
Assistant Examiner—Brian Sines
(74) Attorney, Agent, or Firm—Saliwanchik, Lloyd & Saliwanchik (57) ABSTRACT

A method for the production of a holographic sensor wherein the holographic recording material forming the sensitive element is a polymer matrix, which comprises diffusing into the matrix one or more soluble salts that undergo reaction in situ to form an insoluble sensitive precipitate; and recording a holographic image. This method allows the production of a holographic sensor wherein the holographic recording material forming the sensitive element is an insoluble polymer film.

37 Claims, 5 Drawing Sheets

HOLOGRAPHIC SENSORS AND THEIR PRODUCTION

FIELD OF THE INVENTION

This invention relates to a chemical sensor based on a sensitive element which is a hologram made from a silver halide-based recording material.

BACKGROUND TO THE INVENTION

Many different approaches to producing chemical sensors have been described in the academic and patent literature. There exists a wide range of different transduction mechanisms, which can be married with a suitable chemical or biochemical interface to realise a more or less selective sensor capable of identifying and/or quantitating a particular chemical substance. Transducers that have been successfully applied include those harnessing electrical, acoustic or optical phenomena.

WO-A-9526499 discloses a new class of optical sensor, the holographic chemical sensor, based on a volume hologram. This configuration has the unique feature that the analyte-sensitive matrix film has the optical transducing structure disposed throughout its volume. Because of this physical arrangement of the transducer, the optical signal generated by the sensor is very sensitive to volume changes or structural rearrangements taking place in the analyte sensitive matrix as a result of interaction or reaction with the analyte.

In order to realise a holographic chemical sensor, a hologram must be recorded in a material which responds to a certain chemical or biochemical analyte. To date, however, few suitable holographic film materials exist. The most common type of holographic film is a silver halide-containing gelatin film made by a liquid phase colloid formation technique, followed by coating onto a suitable support layer. This method has been universally adopted for production of ultra-fine grain silver halide film and works well with gelatin as the support polymer. To be successful, this method requires that the polymer that will form the support matrix should be:

soluble in a solvent compatible with silver and halide salts (usually water);

a stabiliser of growing silver halide colloidal particles;

capable of forming a film when cast on a support substrate that is stable; and insoluble under the conditions required to process the film.

Millington et al, Anal. Chem. 67:4229–33 (1995), Millington et al, Sensors and Actuators B33:1–5 (1996), and Blyth et al, Anal. Chem. 68:1089–94 (1996), describe the applications of gelatin-based holographic film to detect water in hydrophobic liquids and proteolytic enzymes such as trypsin.

Another known type of hologram recording material is dichromated gelatin or dichromated polyvinyl alcohol (PVA). These materials contain no silver halide and the holographic image is recorded by a photo-chemical cross-linking process which renders the material harder and less able to be swollen by solvents in regions exposed to light. Subsequent chemical processing produces small air voids in the material, creating a modulation of the refractive index and producing very bright holograms.

A third group of holographic recording materials is the photopolymer materials; see Mannivanen and Lessard, Trends Pol. Sci. 2:282–90 (1994). These vary widely in their composition and mechanisms of hologram recording. The materials from which they are made and their structures render them unsuitable for sensing applications.

In the early days of photography, before the liquid-phase colloid method was introduced, an alternative method for making photosensitive film was introduced by Henry Fox Talbot; see GB-A-0012906 (1849) and GB-A-0013664 (1851). This was subsequently optimised for gelatin film, as described by Liesegang, Phot. Rund. 52:198–200 (1915). In this procedure, a protein film was first made and then treated with silver salt, dried and treated with a halide salt or molecular halogen. The order of exposure to silver ions and halogen could also be reversed.

Very few polymers other than gelatin have the property of being able to stabilise silver halide colloids in solution. Hence gelatin is still universally used in the making of fine-grain silver halide film, despite many attempts within the photographic industry to find viable alternatives, as described by Croome, J. Photo. Sci. 30:181–5 (1982).

Applications of gelatin to chemical sensing are severely restricted by its complex chemical nature and hence the difficulty of chemically derivatising it in a rational way in order to change its analyte selectivity. PVA-based holograms have some advantages over gelatin, but they are still very restricted in their scope, due to the incompatibility between the sensitive silver halide colloidal particles and the conditions required to chemically transform the PVA into a stable and analyte-selective matrix.

Other types of holographic recording material known to those skilled in the art are also unsuitable for a variety of reasons. For example, when holograms made by the dichromating method are immersed in liquid, the voids fill up and the refractive index modulation is lost; hence these materials are entirely unsuitable for use as liquid phase chemical or biochemical sensors. Photopolymer holograms are either uncross-linked or are only cross-linked in the areas of light exposure during hologram recording, and thus are not stable to immersion in solvents of the polymers from which they are made. Such solvent exposure disrupts the ordered layer structure of the hologram. Many photopolymer formulations are also very hydrophobic and hence incompatible with aqueous solutions of analytes, which are incapable of penetrating the hologram.

Due to the problems with other types of holographic recording material, and also because of ease of handling and unrivalled sensitivity to light, silver halide-based films remain the materials of choice for realising holographic chemical sensor devices. However, the liquid phase colloid method is inapplicable to the types of custom-designed polymer materials which are required for analyte-selective chemical sensing. This is because the chemical conditions required to make suitable custom-designed polymer films are not compatible with the silver halide colloid formation process, and often lead to insoluble cross-linked materials.

SUMMARY OF THE INVENTION

The present invention addresses the need for an alternative method of production of silver halide-based holographic recording material. This is achieved by using a sequential treatment technique similar to that described by Talbot, where the polymer film is made first, and the sensitive silver halide particles are added subsequently. This approach is combined with materials that have not previously before used for holographic recording.

According to a first aspect of the present invention, a method for preparing a holographic sensor of the type wherein the holographic recording material forming the analyte-sensitive element is a non-rigid polymer matrix, comprises diffusing soluble salts into the matrix where they react to form an insoluble light-sensitive precipitate with a particle size less than the wavelength of light; a holographic image may then be recorded.

This method can be used to produce volume holograms, of the general type disclosed in WO-A-9526499, suitable for use as sensors. The polymer matrix may be gelatin, but an advantage over the prior art is that other, better defined polymers can also be used. For example, the matrix may be an insoluble polymer film. The matrix may have any of the following advantageous characteristics (many of which are distinct from those of gelatin):

a defined pore volume specific for the analyte or a component thereof;

hydrophobicity;

homogeneity;

inertness with respect to any material reactive with gelatin;

non-charged;

requires processing, during or after formation, that is incompatible with the presence of the photosensitive substance;

cannot stabilise silver halide colloids in solution;

has a structure comprising essentially only regular repeating units.

According to a further aspect of the invention, a sensor for an analyte comprises a hologram supported on or within an insoluble polymer film, wherein at least one optical characteristic of the hologram varies as a result of variation of a physical property occurring throughout the bulk of the matrix.

DETAILED DESCRIPTION OF THE INVENTION

The invention preferably uses as its support a transparent glass or plastics substrate which has been pre-treated or "subbed" to improve the adhesion of the overlying polymer layer which will support the holographic structure. The nature of the pre-treatment depends on the substrate material and the polymer that will overlay it. Many techniques are known to those skilled in the art, including silanisation of glass and U.V., thermal or chemical bonding of thin polymer layers to the surface. The most appropriate method is chosen for the combination of materials being used.

A film of the polymer of interest for a particular sensing application is then deposited on top of the pre-treated substrate. The polymer is typically any that has a regular structure of the type comprising, say, at least 50 or 100 repeating units of the same basic structure in the primary chain, whether a homopolymer or copolymer. Typical polymers for use in this invention are selected from polyvinyl alcohol, polyvinylpyrrolidone, polyhydroxyethyl acrylate, polyhydroxyethyl methacrylate, polyacrylamides, polymethacrylamides, homopolymers or copolymers of polymerisable derivatives of crown ethers, and esters of or co- or terpolymers of polyhydroxyethyl acrylate, polyhydroxyethyl methacrylate, polymethacrylamide or polyacrylamide, optionally with other polymerizable monomers or cross-linkers.

The polymer may be soluble or insoluble. If soluble, it may be deposited as a film by any of the techniques known for this purpose, such as spin-coating, roller-coating or use of metering rods or doctor blades. The polymer solution used for coating may have chemical cross-linking agents included, in order to render the resulting film tough and insoluble after curing, or the dried film may subsequently be immersed in a bath of a cross-linking agent to render it insoluble. A typical example of this procedure comprises coating an aqueous polyvinyl alcohol (PVA) solution containing a small amount of glutaraldehyde and a trace of acid catalyst to make a stable cross-linked PVA film.

In an alternative approach to making the polymer film, a mixture of appropriate polymerisable monomers can be mixed with thermal, U.V. or visible light initiators and optionally with solvents, and polymerised in situ on top of the substrate. Typical examples of this approach utilise co- or ter-polymers of acrylate, methacrylate or acrylamide-based monomers, preferably mixed with a certain amount of cross-linker to give a stable insoluble film capable of supporting a holographic structure within it.

Regardless of the film formation method, and after appropriate curing procedures, a stable polymer film can be obtained, that adheres to the substrate. The dry thickness of the film is typically 5 to 50 $\mu$m, although it could be thicker or thinner if appropriate.

After film formation, the film is optionally washed with a suitable solvent to remove any soluble residues, and may be subjected to further chemical derivatisation steps if appropriate, before proceeding with the incorporation of the photosensitive silver halide particles and construction of the holographic structure within the film.

The polymer film is preferably soaked in a solution of a silver salt. This is typically at a concentration of 0.1 to 0.5M. The solvent used depends on the hydrophobicity of the polymer film. For hydrophilic films, aqueous silver nitrate can be used, but, for more hydrophobic materials, solutions of organic soluble silver salts such as silver perchlorate in solvents such as propan-1-ol give much more efficient penetration into the film and hence better silver density in the resulting holograms. The soaking time depends on the nature of the polymer film and can range from less than a minute to hours.

After soaking in a silver salt, the film is optionally dried. The film is then dipped in a bath containing a halide ion. This and subsequent steps must be carried out under safe lighting. By choice, the halide salt is sodium bromide, but chloride or iodide or a mixture, or lithium or potassium salts, may also be used. A sensitising dye matched to the wavelength of the laser that will be used to record the holograms may be also included in the, say, bromide bath. This can be omitted and the hologram sensitised by a post-treatment in a dye solution, but the photo-sensitivity is generally better if the dye is included with the bromide. The bromide bath is preferably agitated, in order to minimise surface build-up of precipitated silver halide.

Immersion time in the bromide bath is very dependent on material. For some polymers, such as polyacrylamide, the time may be very short, e.g. 15–30 seconds. For most materials, a few minutes is optimal, but some materials require longer. The bromide bath can also optionally contain methanol or another water-miscible solvent. In this case, it will usually be necessary to substitute LiBr for NaBr for solubility reasons. The solvent aids penetration of bromide ions into some types of polymer films such as those made from poly(HEMA).

The order of adding the silver salt and the halide salt to the polymer film can be reversed without significant changes to the results. The order described is preferred because it minimises the amount of expensive silver salts involved.

After removal from the bromide bath, the film is washed in water to remove soluble ions and is then exposed to laser light in an appropriate optical configuration. The film can be exposed wet or dry or in any partially swollen state, depending on the final application and the desired reflection colour of the hologram. The degree of swelling during exposure can be used to tune the colour. The holographic exposure can be made using any of the configurations known to those skilled in the art, but a preferred format is a simple reflection hologram made using a plane mirror as the object.

Following exposure, the hologram is developed using an appropriate developer. This can be selected from the wide range of formulations used in holography. For some materials (particularly more hydrophobic ones), a developer containing methanol gives superior results. After development, the film is washed thoroughly with water.

In most cases, it is desirable to fix the developed hologram to remove residual silver halide. This is most conveniently achieved using sodium thiosulphate solution, with the optional addition of alcohol for more hydrophobic materials. Fixing typically requires about 5 minutes but depends on the nature and thickness of the polymer film.

Finally, the hologram may optionally be bleached. Bleaching makes the hologram near-transparent and is helpful if the transmitted spectrum is measured rather than the reflected spectrum. Appropriate bleaching conditions can be chosen from the range of options familiar to those skilled in holography. The preferred configuration for the novel holographic sensors is to use them in reflection measurements. In this case, it is preferable to leave the holograms unbleached since they are more light-stable in this state.

The completed hologram can be used in any appropriate monitoring format. This could be a transmission or reflection spectrometer device, a dip-stick, a fibre-optic probe or a label. These are given by way of example only.

The design of the polymer material from which the hologram is constructed is the key to the analyte-selective sensing abilities of the final device. Many different design approaches could be applied depending on the target analyte and a few will be described here by way of example, although the scope of the invention should be understood to be very broad and is not limited only to the approaches described below.

One approach is to make the hologram in a natural or synthetic polymer, or a mixture containing one or more such polymer(s), which can be degraded by an enzyme or a group of related enzymes. When the enzyme hydrolyses the polymer, the structural integrity of the polymer film is undermined, and the reflection spectrum of the hologram changes giving a signal. Example 1 (below) describes this approach, using starch to select for an enzyme, α-amylase, which specifically degrades starch chains. By replacing the starch with other carbohydrates, the selectivity would be altered. Thus dextran holograms would select for dextranase and pullulan holograms would select for pullunases and iso-amylases. By using other types of polymers, other classes of enzymes may be targeted, such as proteases.

It is not necessary for the whole of the polymer structure to be degradable by the target enzyme. Only occasional linkages along the main chain of the polymer need to be cleavable, or alternatively, cross-linking sites can be targeted. Example 5 (below) shows how cleavage of the cross-links in a gel structure leads to a signal. This simple chemical example can be extended by designing more complex cross-links, such as ones with peptide spacers containing cleavage sites for specific proteases. These designed synthetic polymer films may thus have specificity for particular proteases.

By coupling short peptide protease substrates to the polymer chains of the film, it may also be possible to create a response by a charge change mechanism. For instance, if the peptide was initially uncharged but created an immobilised charged group when cleaved by the protease, the increase in immobilised charge groups may cause the film to swell, hence generating a response. The converse situation, where a charged group is removed by enzymic cleavage, could also be exploited. In this case, a contraction would be observed. This concept can also be extended to other classes of enzymes using appropriately designed substrates.

The design concepts for holographic sensors are not limited to systems using cleavage mechanisms. If the analyte of interest changes the microenvironment around a particular type of polymer chain, it may cause the polymer chain to change its conformation, leading to a measurable volume change. This is demonstrated by Example 2 (below), where addition of ethanol to a poly(HEMA)-based hologram causes a progressive swelling which can be used to quantitate the amount of ethanol present.

By inclusion of a specific molecular receptor in the polymer structure, volume changes can be induced upon binding of the molecule in question. This is demonstrated in Example 3 (below) where crown ethers are used as receptors that can specifically bind certain types of metal ions. The response can arise by various mechanisms. Osmotic swelling may occur if charged groups are held in the gel by the receptor. Alternatively, if binding of the analyte causes dimerisation of the receptor, this will tend to pull the receptors closer together and cause a contraction of the film. Binding of the analyte in the molecular receptor may also cause twisting of the polymer chains or otherwise alter the local microenvironment within the polymer film such that a measurable volume change results. Materials such as crown ethers may provide a defined pore volume within which specific analytes are received.

More complex polymer materials may also be designed, where the structure is, at least in part, held together by an interaction between an immobilised analyte and a molecular receptor for that analyte. This generates physical cross-links in the polymer structure. Upon introduction of free soluble analyte, this will compete with the immobilised analyte for the binding sites in the molecular receptor, leading to a reduction in the physical cross-linking of the film and consequently to swelling. This approach may be used with a range of materials and analytes, particularly for antigen/antibody interactions, ligand/binding protein interactions (e.g. glucose with concanavalin A), and interactions of designed artificial receptors with analytes.

For realisation of the many designed materials that could be created for measuring particular analytes, the in situ polymerisation approach described above is preferred, because of the ability to control and design the properties of the resulting polymer film. Specially designed immobilised substrates, receptor molecules, cross-linkers etc. can easily be synthesised and incorporated into films by copolymerisation with other suitable monomers. The degree of swelling can be controlled by alteration of the concentrations of monomers or cross-linkers in the system; hence the behaviour of a hologram can be fine-tuned to match the application, for example with respect to sensitivity and dynamic range. This approach is demonstrated in Example 4 (below), where the pH range over which the sensor operates and the size of the sensor response to a given pH change are both controlled by altering the amount and nature of the ionising species incorporated into the polymer film. Although the in situ polymerisation method is preferable in many cases, other techniques are appropriate for some materials and the scope of the invention is not limited to this approach.

The following Examples further illustrate the invention.

Example 1

An Amylase Sensor

Starch gratings have the potential to be used as biosensors to detect the concentration of the digestive enzyme alpha-amylase in a body fluid. This can be vitally important as an indication of acute pancreatitis. However starch does not lend itself to the production of ultra-fine grain photographic emulsion when using the conventional technique with gelatin, because it causes severe grain growth before the gelation occurs.

Five steps are described for preparing and using the sensor. These are:

1. The treatment of glass to take a starch coating.
2. The preparation and coating of a layer of starch.
3. The introduction of a light-sensitive fine grain silver halide deposit in the pre-coated starch layer by a diffusion process.
4. Exposure and development to record an optical hologram.
5. Use of the starch hologram as a sensor for amylase.

Step 1
Presubbing coating:
Solution A

| | |
|---|---|
| 50 ml | deionised (DI) water |
| 0.6 g | potato starch hydrolysed for electrophoresis (Sigma) |
| 0.6 g | Agarose Type A 0169 (Sigma) |

The powdered carbohydrates are added to the cold water and stirred on a heater until the temperature reaches about 90° C. The mixture then becomes clear and free of any solid powder.

Solution B

| | |
|---|---|
| 0.10 g | ammonium dichromate crystals |
| 10 ml | DI water |

Solution B is added to Solution A to form a solution for a spin coating.

Clean microscope slide glass is then put in a standard laboratory spin coater and about 1 ml of the solution is pipetted onto the centre of the slide. The spin rate is adjusted to give a thickness of no more than 1 μm. The lighting conditions during this part of the operation should be yellow or free of blue light.

The coating is thin, since a thicker layer may later cause a significant amount of holographic grating to be created in the sublayer. This would then create spurious diffraction effects which might be confused with the diffraction from the starch overlayer which should always be substantially thicker than the sublayer.

The spin-coated material is dry within a minute or even a few seconds. Such spun coated slides are then exposed to a source of strong ultraviolet light for a time sufficient to cause all the ammonium dichromate in the film to crosslink the starch/agarose mix onto the glass slide. It is particularly important that the UV or violet light first passes through the glass side rather than through the film surface.

Step 2

2.0 g potato starch hydrolysed for electrophoresis (Sigma) and 24 g water are heated to 90° C. and stirred until clear. 1.0 ml 10% glutaric dialdehyde solution is added after the solution has cooled to about 50° C.

A relatively thick layer of coating is required on the subbed slides. A number of the subbed slides were lined up without gaps on a horizontal surface and a warmed wire-wound Meyer bar is used (7 turns of wire per centimeter) to govern the coating thickness. The coating is then dried in a tepid air flow and the dry coating is heated at 116 C. for 1 hour, to obtain the necessary degree of crosslinking to enable a stable holographic grating to be formed after the treatment detailed below.

Step 3

Approx 1 ml of a 0.25M solution of silver nitrate is placed on a clean flat surface and a starch-coated slide is pressed face down onto the droplet. The solution then covers the starch coating by surface tension. The solution is left to soak into the starch layer for 2 minutes. It is then removed, and surface liquid on the slide is removed by using filter paper as blotting paper. The slide is then dried for a minute in a strong warm air flow.

36 g lithium bromide is stirred until dissolved in 900 ml water. This is poured into 0.10 g sensitising dye that has been stirred into and dissolved in 300 ml methanol, in a 2 liter beaker and the solution is given a rapid rotation with a magnetic stirrer. The dried slide is held in the rotated solution for a certain time. For convenience this time will be called t(Br); depending on the conditions, its value may be changed.

The starch coating is successfully impregnated with silver halide (in this case AgBr) if t(Br) is 1 minute. If t(Br) is too long, then grain growth can become a problem, but if t(Br) is too short, then the penetration can be insufficient to obtain a later satisfactory gratin. After removing the slide from the bromide bath, it is at once washed under running water.

If the dye is 1,1-diethyl-2,2'-cyanine iodide, then the slide will be sensitized for exposure to a frequency-doubled YAG laser at 532 nm wavelength. If the dye is pinacyanol bromide, then the slide will be sensitized to the 633 nm red from a HeNe laser. The dye does not have to be in the solution of bromide ion at this point but may instead be used in a separate bath after the precipitation of silver bromide has taken place within the coated layer. However, by including the dye in the bromide ion bath, it causes a high light-sensitivity which has been found not to be so achievable if the dye bath is used separately.

The lithium bromide salt may be fully or partially replaced by equimolar equivalents of other halides (not fluorides) such as LiCl or LiI. This will produce various alterations of the nature of the precipitated silver salt within the body of the coated layer. Also, in this particular example, all the lithium bromide may be replaced by sodium bromide.

Step 4

The object used to make the hologram is a plain or curved mirror. The starch-coated plate, preferably in a swollen state, is placed close to the mirror and a diverged laser beam is passed through the coating so that it hits the mirror and is then reflected back through the coating, thus causing an interference pattern in the form of standing waves. This is recorded as a volume hologram with the interference fringes running roughly parallel to the plane of the film (like pages in a book). This principle is well known to those familiar with holographic practices.

After exposure of the slide to the holographic recording conditions, preferably under water or other suitable liquid, the hologram is developed in standard developers such as those detailed in Practical Holography by Graham Saxby, published by Prentice Hall. The development can be stopped by a 10% aqueous solution of acetic acid. Undeveloped silver halide can then be removed in a 15% Hypo solution.

Step 5

The finished, processed and washed grating is cut to fit in a spectrophotometer cuvette. The liquid or sample to be tested for amylase content is added to the tube which should also contain appropriate buffers to facilitate the enzyme reaction on the starch grating. The speed of attack at a given temperature is then monitored by recording one of the characteristic changes to the reflection spectrum of the hologram as a function of time. This can be related to the concentration of amylase in the original sample.

Figure 1:
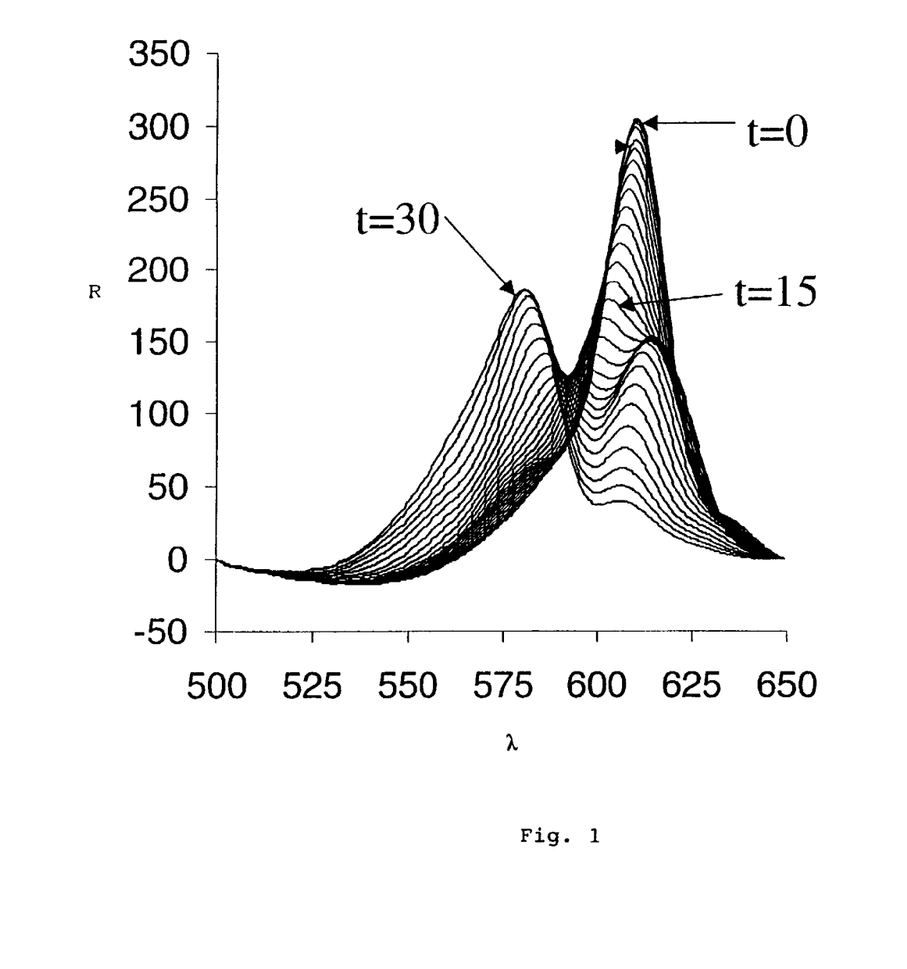

FIG. 1 shows the effect of α-amylase on the hologram. More specifically, the graph of reflectance (R) against wavelength ($\lambda$; nm) shows degradation of the hologram. The traces are at 1 minute intervals, after the addition of 500 units amylase.

This approach may be extended to a wide range of other hydrolytic enzymes if the starch hologram is replaced by one made in a different polymer material which is cleavable by the enzyme of interest.

Example 2

An Ethanol Sensor

A microscope slide is presubbed as follows: a 1% solution of 3-(trimethoxysilyl)propyl methacrylate in dry acetone is poured over it and left overnight to evaporate and hydrolyse on the glass surface. Excess silane is removed by washing with acetone before drying.

A solution of polymerizable monomers is prepared as follows:

| | |
|---|---|
| 475 µl | 2-Hydroxyethyl methacrylate (HEMA) |
| 25 µl | Ethylene dimethacrylate (EDMA) |
| 500 µl | Propan-1-ol |
| 5 mg | 2,2'-dimethoxyphenyl acetophenone (DMPAP) |

100 µl of this solution is poured onto a subbed slide (laid horizontally) and covered with an inert sheet of non-stick as high density polythene of the type used for transfer lettering (Letraset). The sandwich is then exposed to UV light through the glass side until fully polymerised. After removing the polythene cover sheet, the sample is rinsed in methanol and dried in a warm air flow.

The sample is treated with silver nitrate as for Example 1, but this time it is necessary for the 0.25 M silver nitrate to be in 50% water/50% 2-propanol to enable it to readily penetrate the polymer. The slide is left in contact with the solution for an hour (even several hours was not found to be detrimental or to make any difference).

After blotting the surface and drying as before, the slide is clamped and held in a rapidly rotating solution of bromide ions made up as follows:

| | |
|---|---|
| 850 ml | Methanol |
| 0.03 g | Sensitizing dye [see Example 1] | stirred until dissolved, then are added:

| | |
|---|---|
| 150 ml | Water |
| 27 g | Lithium bromide |

In this case immersion time t(Br) is 10 minutes. The slide is then rinsed in running water.

After exposure, a developer formulation containing a large percentage of alcohol is used:

| | |
|---|---|
| 25 g | Sodium hydroxide |
| 150 ml | Water |
| 10 g | Hydroquinone |
| 850 ml | Methanol |

The development is stopped in a bath of:

| | |
|---|---|
| 50 ml | Acetic acid |
| 150 ml | Water |
| 800 ml | Methanol |

The grating consists at this stage of developed silver fringes and it can be advantageous to remove undeveloped silver bromide in a "fix". A fix solution is 10% "hypo" (sodium thiosulphate) in a 50/50 solution of methanol/water. After agitating in hypo solution for 10 minutes, residual dye in the emulsion is also removed.

Figure 2:
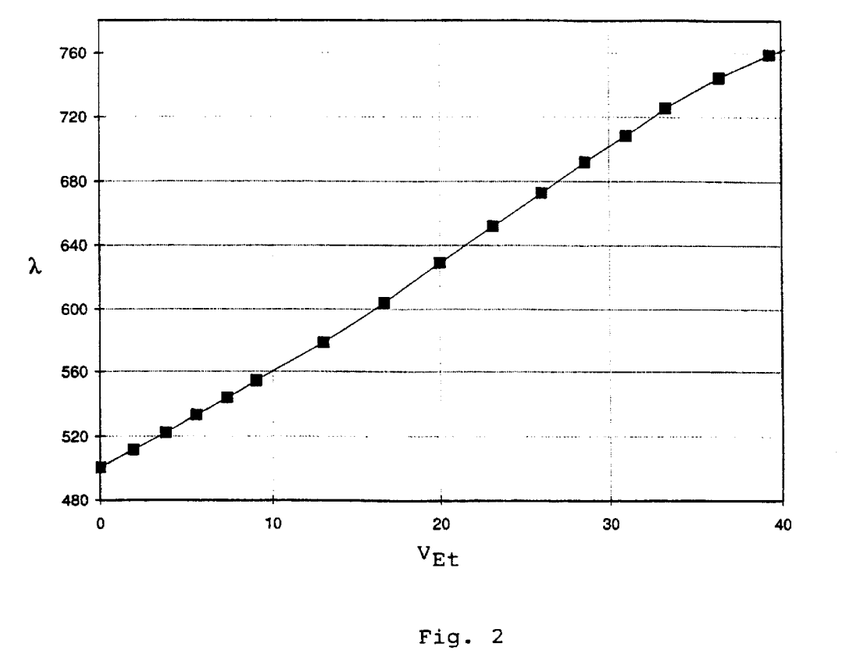

FIG. 2 is a graph of wavelength ($\lambda$; nm) against ethanol ($V_{E1}$; vol %). It shows the change in volume of this hologram as it is immersed in mixtures of ethanol and water. It can therefore he used as a sensor to monitor concentrations of ethanol.

Example 3

Na/K Sensors

Sensors capable of measuring the concentration of sodium ions in the presence of potassium ions and vice versa are made.

| | |
|---|---|
| 3 mg | DMPAP dissolved in 70 µl methanol [UV initiator] |
| 50 µl | HEMA |
| 75 µl | methacryloyl ester of hydroxymethyl 12 crown 4 |

The liquid solution is poured over a presubbed microscope slide and the same treatment is carried out as in Example 2, to produce a grating which can be cut to suit a spectrometer cuvette or mounted at the end of a fibre optic cable. Thus the silver grating is embedded in a copolymer of methacryloyl 12 crown 4 and HEMA in the approximate mole ratio of 60:40. Since the grating is subjected to high concentrations of salt solutions during preparation, it first requires extensive rinsing in several changes of de-ionized water for at least an hour before it can be used as a sensor.

Figure 3A:
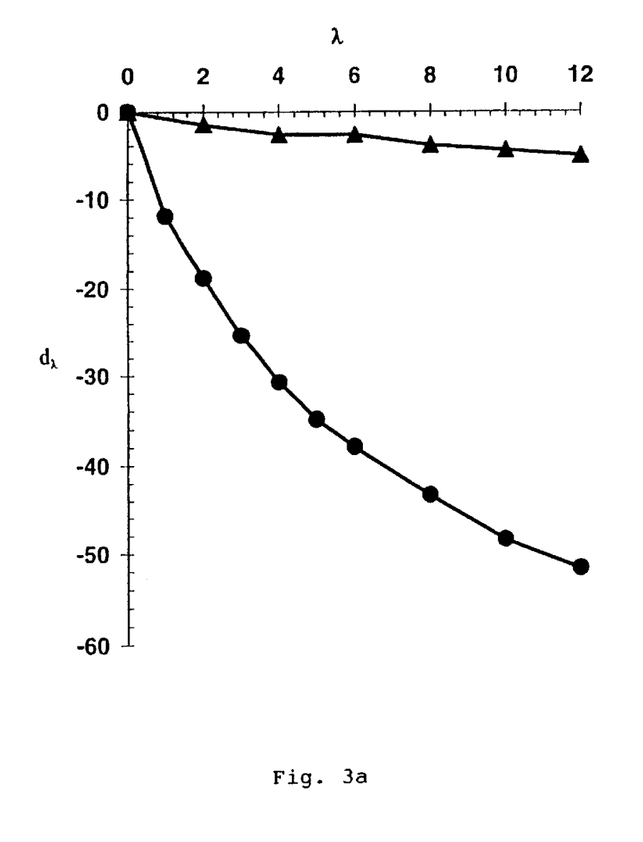

FIG. 3$a$ is a graph of cation concentration ([+]; mM) against wavelength shift ($d_\lambda$; nm). It contrasts the effects of sodium ions (●) and potassium ions (▲) on the response of the hologram.

Figure 3B:
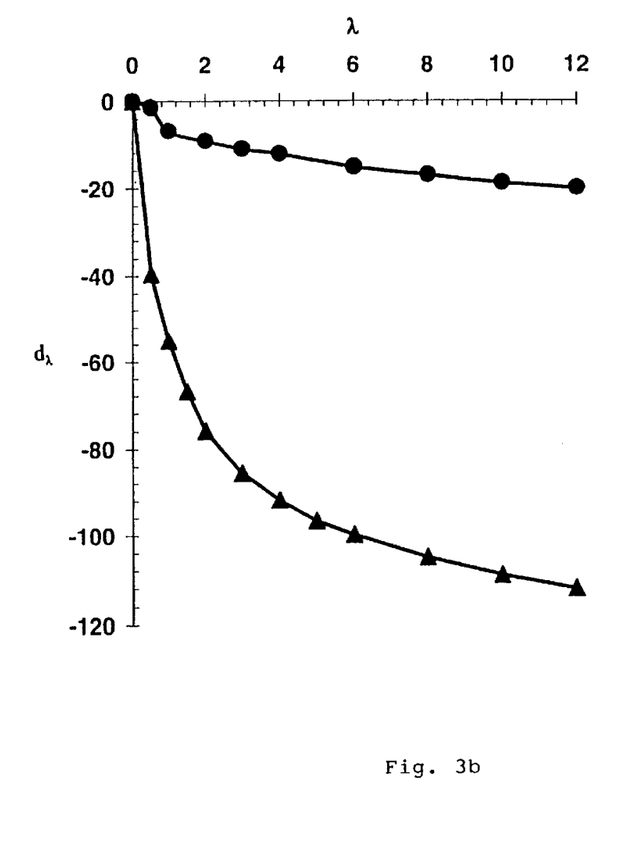

By the same general procedure, but using the converse effect, a sensor capable of measuring potassium ions in the presence of sodium ions can be made by using a larger crown ether ring. Thus, if the 12 crown 4 compound is substituted by an equivalent quantity of the equivalent 15 crown 5 compound, the resulting grating can act as a potassium ion sensor. This is shown in FIG. 3b.

Example 4

A pH sensor

Sensors capable of measuring the pH of a liquid over a particular range are prepared in a similar manner to Example 2, but incorporating functional monomers, which ionise over a particular pH interval. In this case, methacrylic acid (MAA) and vinyl pyridine (VP) are used. MAA is an acid and is uncharged at low pH. It ionises and becomes charged as the pH is raised. VP is charged at low pH and loses its charge as the pH is raised.

The monomer compositions used to make the films are shown in the following table:

| Identifier | HEMA (µl) | EDMA (µl) | MAA (µl) | VP (µl) | propan-1-ol (µl) | DMPAP (mg) |
|---|---|---|---|---|---|---|
| — | 475 | 25 | 0 | 0 | 500 | 5 |
| 2% MAA | 465 | 25 | 10 | 0 | 500 | 5 |
| 4% MAA | 455 | 25 | 20 | 0 | 500 | 5 |
| 6% MAA | 445 | 25 | 30 | 0 | 500 | 5 |
| 8% MAA | 435 | 25 | 40 | 0 | 500 | 5 |
| 10% MAA | 425 | 25 | 50 | 0 | 500 | 5 |
| 2% VP | 465 | 25 | 0 | 10 | 500 | 5 |
| 4% VP | 455 | 25 | 0 | 20 | 500 | 5 |
| 6% VP | 445 | 25 | 0 | 30 | 500 | 5 |
| 8% VP | 435 | 25 | 0 | 40 | 500 | 5 |
| 10% VP | 425 | 25 | 0 | 50 | 500 | 5 |

100 µl of each formulation is placed on a pre-subbed slide, covered with a polymer overlay and polymerised with U.V. light. The overlay is removed, and each slide is washed with methanol. 100 µl 0.3M silver perchlorate in propan-1-ol:water (1:1) is placed on each slide, which is covered with a polyester overlay to spread the liquid over the whole slide area. This is left for 5 minutes, then the overlay is removed, the surface blotted and the slide dried in warn air. Each slide is dipped in a bromide bath as described in Example 2. t(Br) was 2 minutes. After dipping, the slide is washed in running water.

During holographic exposure, it is important that the functional groups are in their non-ionised form so that the subsequent replay wavelength remains visible at all pH values. Hence MAA-containing films are exposed immersed in 1% ascorbic acid, pH3, and VP-containing films in 0.1M phosphate buffer, pH7.2. Development is with the methanolic hydroquinone developer described in Example 2.

Figure 4A:
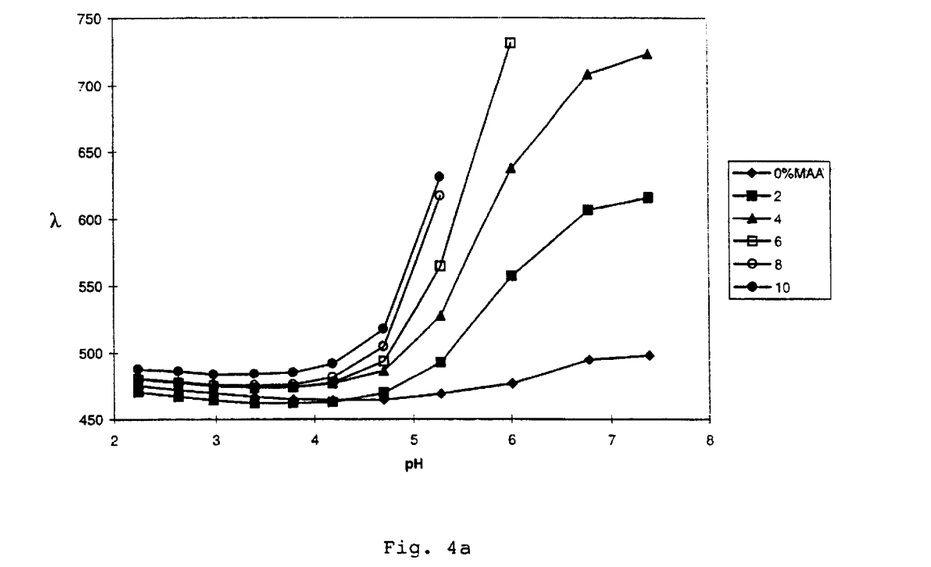
Figure 4B:
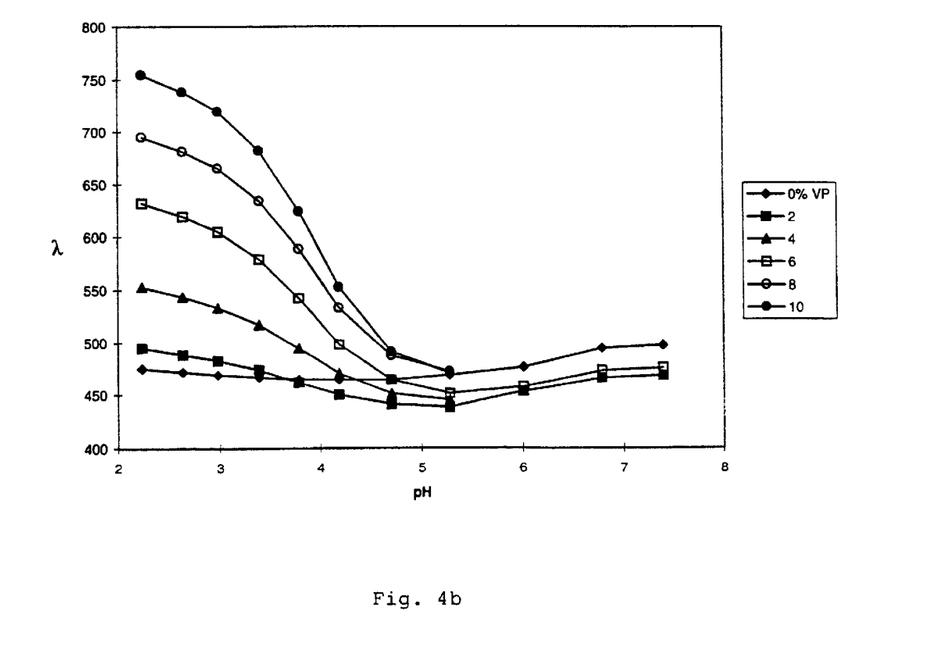

The holograms produced are tested in a series of citrate/phosphate buffers with conductivity normalised to 20 mS/cm using KCl. The responses of the MAA-containing holograms are shown in FIG. 4a and those for VP-containing holograms in FIG. 4b. These graphs are each of wavelength ($\lambda$; nm) against pH. It is clear that the pH interval over which the hologram responds can be changed by altering the nature of the ionising functional group in the hologram. The size of the response, for a given change in pH, can be controlled by altering the amount of ionising monomer in the hologram.

Example 5

A Periodate Sensor

170 µl of 25% w/w methacrylamide in water and 284 µl of 50% w/w acrylamide in water are mixed. 11.56 mg methylene bisacrylamide was added and dissolved, followed by 50 µl of a 4% w/w solution in water of a thioindigo vat dye in its leuco form. 100 µl of this mixture is placed on a pre-subbed slide and polymerised as for Example 2.

This is repeated twice, substituting for the methylene bisacrylamide for 14.55 mg N,N'-bisacryloylpiperazine and 15 mg 1,2-dihydroxyethylenebisacrylamide respectively.

The films are treated to introduce silver nitrate as for Example 1 and then dipped in a bromide bath as for Example 2. t(Br) is 1 minute. The films are exposed, immersed in water and developed and fixed as for Example 1.

Figure 5:
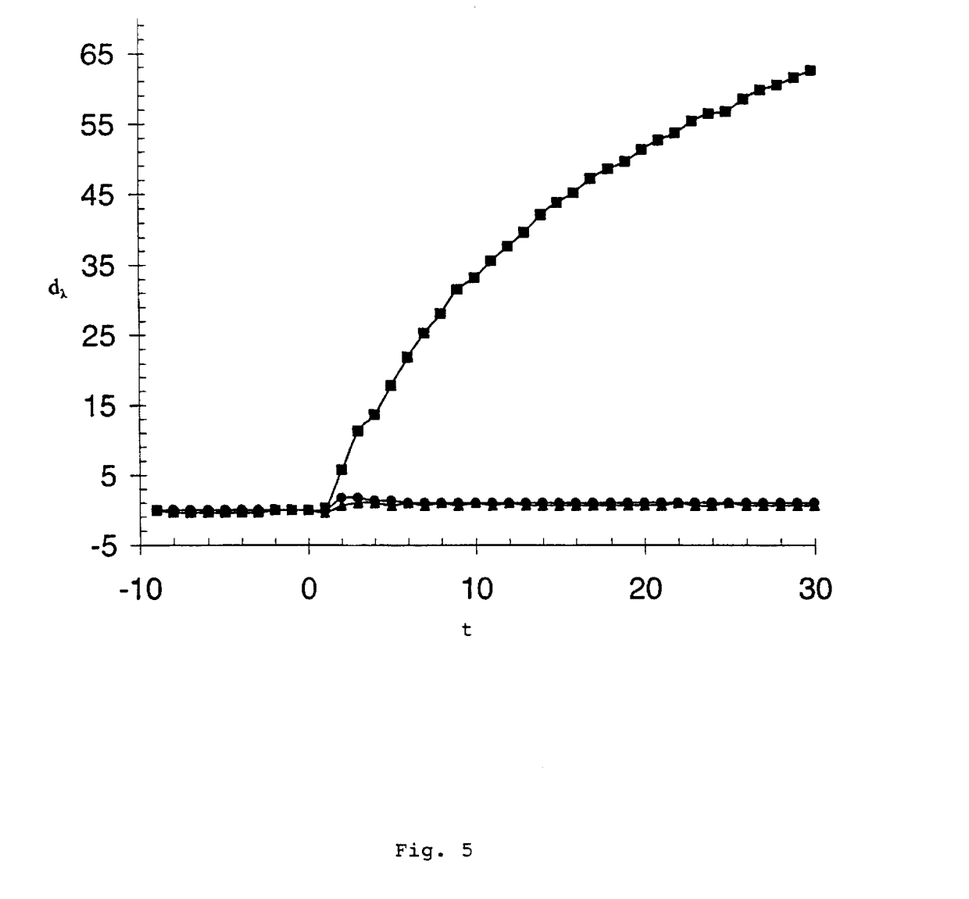

The resulting holograms are cut and placed in 1 ml water in cuvettes. The wavelength is monitored at 1 minute intervals for 10 minutes. Then 10 µl 0.1M NaIO$_4$ is added and the response monitored for 30 minutes. The results are presented in FIG. 5, a graph of wavelength shift ($d_\lambda$; nm) against time (t; min). It is clear that the methylenebisacrylamide (●) and N,N'-diacryloylpiperazine (▲) cross-linked holograms are unaffected by this treatment, but that the 1,2-dihydroxyethylenebisacrylamide-containing hologram (■) is caused to swell by the cleavage of the vicinal diol functionality in the cross-linker by the periodate anion. Hence the presence of periodate can be measured by the hologram.

This Example can be extended by implication to any other chemically or biochemically cleavable cross-linker built into an otherwise more or less inert polymer film.

What is claimed is:

1. A method for the production of a holographic sensor wherein the holographic recording material forming the sensitive element is a polymer matrix, said method comprising providing the polymer matrix; diffusing into the polymer matrix one or more soluble salts that undergo reaction in situ to form an insoluble photosensitive precipitate; and recording a holographic image.

2. The method according to claim 1, wherein the polymer is a natural polymer.

3. The method according to claim 2, wherein the polymer is gelatin, starch or agarose.

4. The method according to claim 1, wherein the polymer is a synthetic polymer.

5. The method according to claim 4, wherein the polymer is selected from the group consisting of polyvinyl alcohol; polyvinylpyrrolidone; polyhydroxyethyl acrylate; polyhydroxyethylmethacrylate; polyacrylamides; polymethacrylamides; homopolymers, or copolymers, or polymerisable derivatives of crown ethers; and esters of, or co- or terpolymers of, polyhydroxyethylacrylate, polyhydroxyethylmethacrylate, polymethacrylamide and polyacrylamide; optionally with other polymerizable monomers or cross-linkers.

6. The method according to claim 1, wherein the polymer matrix is cross-linked.

7. The method according to claim 1, which additionally comprises, during a prior step of forming the polymer, incorporating a component of the reaction in the polymer.

8. The method according to claim 1, which additionally comprises incorporating in the sensor a photosensitizing dye, whereby the spectral sensitivity is enhanced over a particular range of wavelengths.

9. The method according to claim 1, wherein the photosensitive precipitate is a silver halide.

10. The method according to claim 9, wherein the one or more soluble salts comprises a silver salt and the reaction comprises immersing the matrix in a solution of a halide salt, optionally after drying the matrix.

11. The method according to claim 9, wherein the one or more soluble salts comprises a halide salt, and the reaction comprises immersing the matrix in a solution of a silver salt, optionally after drying the matrix.

12. The method according to claim 1, wherein the matrix interacts with its physical or chemical environment to create an optical response which is a change in the optical properties of the hologram.

13. The method according to claim 12, wherein the optical response arises from a volume change in the matrix as a result of its interaction with an analyte or group of analytes.

14. The method according to claim 12, wherein the optical response arises from degradation or re-ordering of the matrix as a result of its interaction with an analyte or group of analytes.

15. The method according to claim 12, wherein the optical response arises from a change in the distribution of refractive index within the matrix as a result of its interaction with an analyte or group of an analytes.

16. The method according to claim 1, wherein the precipitate is of particles that have a grain size not more than 100 nm.

17. The method according to claim 16, wherein the grain size is less than 50 nm.

18. A sensor for an analyte, the sensor comprising a hologram supported within a polymer matrix, wherein at least one optical characteristic of the hologram varies as a result of variation of a physical property occurring throughout the bulk of the matrix, characterized in that the polymer matrix is an insoluble polymer film.

19. The sensor according to claim 18, wherein the matrix is a synthetic polymer, e.g. a homopolymer or a copolymer of repeating monomer units.

20. The sensor according to claim 18, wherein the photosensitive substance is a salt.

21. The sensor according to claim 18, wherein the polymer is a natural polymer.

22. A method for the detection of an analyte in a sample, which comprises contacting the sample with a sensor comprising a hologram supported within a polymer matrix, wherein at least one optical characteristic of the hologram varies as a result of variation of a physical property occurring throughout the bulk of the matrix, characterized in that the polymer matrix is an insoluble polymer film, and observing an optical characteristic of the hologram on the application of light.

23. The method according to claim 22, wherein the photosensitive particles have a grain size not more than 1/10 of the wavelength of the incident light.

24. The sensor, according to claim 18, wherein the polymer is gelatin, starch or agarose.

25. The sensor, according to claim 18, wherein the polymer is a synthetic polymer.

26. The sensor, according to claim 25, wherein the polymer is selected from the group consisting of polyvinyl alcohol; polyvinylpyrrolidone; polyhydroxyethyl acrylate; polyhydroxyethyl methacrylate; polyacrylamides; polymethacrylamides; homopolymers, or copolymers, of polymerisable derivatives of crown ethers; and esters of, or co- or terpolymers of, polyhydroxyethylacrylate, polyhydroxyethylmethacrylate, polymethacrylamide and polyacrylamide; optionally with other polymerizable monomers or cross-linkers.

27. The Sensor, according to claim 18, wherein the polymer matrix is cross-linked.

28. The sensor, according to claim 18, further comprising a photosensitizing dye, whereby the spectral sensitivity is enhanced over a particular range of wavelengths.

29. The sensor, according to claim 18, wherein the photosensitive precipitate is a silver halide.

30. The sensor, according to claim 18, wherein the one or more soluble salts comprises a silver salt.

31. The sensor, according to claim 18, wherein the one or more soluble salts comprises a halide salt.

32. The sensor, according to claim 18, wherein the matrix interacts with its physical or chemical environment to create an optical response which is a change in the optical properties of the hologram.

33. The sensor, according to claim 32, wherein the optical response arises from a volume change in the matrix as a result of its interaction with an analyte or group of analytes.

34. The sensor, according to claim 32, wherein the optical response arises from degradation or re-ordering of the matrix as a result of its interaction with an analyte or group of analytes.

35. The sensor, according to claim 32, wherein the optical response arises from a change in the distribution of refractive index within the matrix as a result of its interaction with an analyte or group of analytes.

36. The sensor, according to claim 18, wherein the precipitate is of particles that have a grain size not more than 100 nm.

37. The sensor, according to claim 36, wherein the grain size is less than 50 nm.

* * * * *

UNITED STATES PATENT AND TRADEMARK OFFICE
CERTIFICATE OF CORRECTION

PATENT NO. : 6,689,316 B1
DATED : February 10, 2004
INVENTOR(S) : Jeffrey Blyth et al.

It is certified that error appears in the above-identified patent and that said Letters Patent is hereby corrected as shown below:

Column 13
Line 22, "polymer matrix, wherein" should read -- polymer matrix comprising a photosensitive substance, wherein --.
Line 26, "polymer film." should read -- polymer film, and wherein the matrix has opposed faces and the photosensitive substance is disposed at a decreasing density from one opposed face to the other opposed face --.
Lines 32-33, "21. The sensor according to claim 18, wherein the polymer is a natural polymer"; this claim was cancelled.
Line 34, "22. A method" should read -- 21. A method --.
Lines 36-37, "polymer matrix, wherein" should read -- polymer matrix comprising a photosensitive substance, wherein --.
Line 40, "polymer film, and observing" should read -- polymer film, and wherein the matrix has opposed faces and the photosensitive substance is disposed at a; decreasing density from one opposed face to the other opposed face, and observing --.
Line 43, "23. The method according to claim 22," should read -- 22. The method according to claim 21, --.
Line 46, "24. The sensor," should read -- 23. The sensor, --.

Column 14
Line 1, "25. The sensor," should read -- 24. The sensor. --.
Line 3, "26. The sensor, according to claim 25," should read -- 25. The sensor, according to claim 24, --.
Lines 9-10, "polyhydroxyethylacrylate, polyhydroxyethylmethacrylate," should read -- polyhydroxyethyl acrylate, polyhydroxyethyl methacrylate --.
Line 13, "27. The Sensor," should read -- 26. The sensor, --.
Line 15, "28. The sensor," should read -- 27. The sensor, --.
Line 18, "29. The sensor," should read -- 28. The sensor, --.
Line 19, "precipitate" should read -- substance --.
Lines 20-21, "30. The sensor, according to claim 18, wherein the one or more soluble salts" should read -- 29. The sensor, according to claim 18, wherein the photosensitive substance --.
Line 22, "31. The sensor," should read -- 30. The sensor, --.
Lines 22-23, "one or more soluble salts" should read -- photosensitive substance --.
Line 24, "32. The sensor," should read -- 31. The sensor, --.
Line 28, "33. The sensor, according to claim 32," should read -- 32. The sensor, according to claim 31, --.
Line 31, "34. The sensor, according to claim 32," should read -- 33. The sensor, C according to claim 31, --.
Line 35, "35. The sensor, according to claim 32," should read -- 34. The sensor, according to claim 31, --.

UNITED STATES PATENT AND TRADEMARK OFFICE
CERTIFICATE OF CORRECTION

PATENT NO. : 6,689,316 B1
DATED : February 10, 2004
INVENTOR(S) : Jeffrey Blyth et al.

It is certified that error appears in the above-identified patent and that said Letters Patent is hereby corrected as shown below:

Column 14 (cont'd),
Line 39, "36. The sensor," should read -- 35. The sensor, --.
Lines 39-40, "precipitate is of particles" should read -- photosensitive substance comprises particles --.
Line 42, "37. The sensor, according to claim 36," should read -- 36. The sensor, according claim 35, --.

Signed and Sealed this

Twenty-fourth Day of August, 2004

JON W. DUDAS
*Director of the United States Patent and Trademark Office*

UNITED STATES PATENT AND TRADEMARK OFFICE
CERTIFICATE OF CORRECTION

PATENT NO. : 6,689,316 B1
DATED : February 10, 2004
INVENTOR(S) : Jeffrey Blyth et al.

It is certified that error appears in the above-identified patent and that said Letters Patent is hereby corrected as shown below:

Column 13
Line 22, "polymer matrix, wherein" should read -- polymer matrix comprising a photosensitive substance, wherein --.
Line 26, "polymer film." should read -- polymer film, and wherein the matrix has opposed faces and the photosensitive substance is disposed at a decreasing density from one opposed face to the other opposed face --.
Lines 32-33, "21. The sensor according to claim 18, wherein the polymer is a natural polymer"; this claim was cancelled.
Line 34, "22. A method" should read -- 21. A method --.
Lines 36-37, "polymer matrix, wherein" should read -- polymer matrix comprising a photosensitive substance, wherein --.
Line 40, "polymer film, and observing" should read -- polymer film, and wherein the matrix has opposed faces and the photosensitive substance is disposed at a; decreasing density from one opposed face to the other opposed face, and observing --.
Line 43, "23. The method according to claim 22," should read -- 22. The method according to claim 21, --.
Line 46, "24. The sensor," should read -- 23. The sensor, --.

Column 14
Line 1, "25. The sensor," should read -- 24. The sensor. --.
Line 3, "26. The sensor, according to claim 25," should read -- 25. The sensor, according to claim 24, --.
Lines 9-10, "polyhydroxyethylacrylate, polyhydroxyethylmethacrylate," should read -- polyhydroxyethyl acrylate, polyhydroxyethyl methacrylate --.
Line 13, "27. The Sensor," should read -- 26. The sensor, --.
Line 15, "28. The sensor," should read -- 27. The sensor, --.
Line 18, "29. The sensor," should read -- 28. The sensor, --.
Line 19, "precipitate" should read -- substance --.
Lines 20-21, "30. The sensor, according to claim 18, wherein the one or more soluble salts" should read -- 29. The sensor, according to claim 18, wherein the photosensitive substance --.
Line 22, "31. The sensor," should read -- 30. The sensor, --.
Lines 22-23, "one or more soluble salts" should read -- photosensitive substance --.
Line 24, "32. The sensor," should read -- 31. The sensor, --.
Line 28, "33. The sensor, according to claim 32," should read -- 32. The sensor, according to claim 31, --.
Line 31, "34. The sensor, according to claim 32," should read -- 33. The sensor, according to claim 31, --.
Line 35, "35. The sensor, according to claim 32," should read -- 34. The sensor, according to claim 31, --.

UNITED STATES PATENT AND TRADEMARK OFFICE
CERTIFICATE OF CORRECTION

PATENT NO.    : 6,689,316 B1
DATED         : February 10, 2004
INVENTOR(S)   : Jeffrey Blyth et al.

It is certified that error appears in the above-identified patent and that said Letters Patent is hereby corrected as shown below:

Column 14 (cont'd),
Line 39, "36. The sensor," should read -- 35. The sensor, --.
Lines 39-40, "precipitate is of particles" should read -- photosensitive substance comprises particles --.
Line 42, "37. The sensor, according to claim 36," should read -- 36. The sensor, according claim 35, --.

This certificate supersedes Certificate of Correction issued August 24, 2004.

Signed and Sealed this

Seventh Day of December, 2004

JON W. DUDAS
*Director of the United States Patent and Trademark Office*